United States Patent
Smedegaard

(12) 
(10) Patent No.: US 6,231,540 B1
(45) Date of Patent: May 15, 2001

(54) INJECTION MEMBER

(75) Inventor: Jørgen K. Smedegaard, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/112,494

(22) Filed: Jul. 9, 1998

Related U.S. Application Data
(60) Provisional application No. 60/053,496, filed on Jul. 23, 1997.

(30) Foreign Application Priority Data

Jul. 14, 1997 (DK) .................................... 0861/97

(51) Int. Cl.[7] .............................. A61M 5/30; A61M 5/31; A61M 5/32
(52) U.S. Cl. ............................. 604/68; 604/117; 604/71; 604/239; 604/272
(58) Field of Search .................... 604/68, 69, 70, 604/71, 117, 118, 310, 890.1, 46–47, 272, 239, 3

(56) References Cited

U.S. PATENT DOCUMENTS

| | | | |
|---|---|---|---|
| 2,704,542 | * 3/1955 | Scherer | 128/173 |
| 3,507,276 | * 4/1970 | Burgess | 128/173 |
| 3,964,482 | * 6/1976 | Gerstel et al. | 128/260 |
| 4,235,234 | * 11/1980 | Whitney et al. | 128/216 |
| 5,505,694 | * 4/1996 | Hubbard et al. | 604/51 |
| 5,569,189 | * 10/1996 | Parsons | 604/68 |
| 5,954,689 | * 9/1999 | Poulsen . | |
| 6,056,716 | * 5/2000 | D'Antonio et al. . | |

* cited by examiner

Primary Examiner—Angela D. Sykes
Assistant Examiner—Patricia Bianco
(74) Attorney, Agent, or Firm—Steve T. Zelson, Esq.

(57) ABSTRACT

An injection member for a jet spray injection device through which device a dose of medicine is administered for subcutaneous or intramuscular injection has a jet nozzle designed as a skin-penetrating member having a length of 0.05–0.3 mm enabling it just to penetrate the stratum corneum.

8 Claims, 1 Drawing Sheet

INJECTION MEMBER

CROSS-REFERENCE TO RELATED APPLICATIONS

This application claims priority under 35 U.S.C. § 119 of Danish application Serial No. 0861/97, filed Jul. 14, 1997, and of U.S. provisional application No. 60/053,496, filed Jul. 23, 1997, the contents of which are fully incorporated herein by reference.

STATEMENT REGARDING FEDERALLY SPONSORED RESEARCH OR DEVELOPMENT

Not Applicable

BACKGROUND OF THE INVENTION

The invention relates to an injection member for a jet spray injection device through which device a dose of medicine is administered for subcutaneous or intramuscular injection.

It is often wanted to perform a subcutaneous injection of a medicine dose. The medicine is deposited in the subcutis tissue from where it subsequently finds its way to the blood. Especially diabetics have to frequently inject themselves with insulin to keep their blood glucose content under control. For this purpose a number of injection devices exist.

A conventional injection device comprises a syringe which is provided with a needle which has a length enabling it to penetrate the cutis and enter the subcutis where a dose of medicine is deposited by being pressed from the syringe out through the needle.

However, many people are reluctant to prick themselves with needles and although needles are made very thin and short an injection may still engender the above mention reluctance which may promote a user to cut down the number of injections to a level beyond the warrantable.

To overcome this needle phobia of the patient and to further reduce pain, various jet injection systems have been developed. Such jet injection systems have no needle, but instead use a spray nozzle through which the medicine is sprayed to give the medicine a speed enabling it to penetrate the cutis and be dispersed in the subcutis. However, dosing is difficult, in part due to the anatomical condition of the skin (cutis) where the first layer (stratum corneum) consists of dead keratinized cells. The layer is much more resistant to water penetration than to lipid penetration, and it forms a strong mechanical barrier, especially considering the thickness of the layer, which has a mean of 0.1 mm on the most of the body (thin skin). The stratum corneum is enlarged in a few specific areas (thick skin): e.g., the hand and the foot sole areas where injection normally is avoided. Beneath the stratum corneum lie various other layers of epidermis, with living skin cells, blood vessels, sensory nerve endings etc. Three epidermis is followed by the dermis which is mainly connective tissue. Then follows the subcutis (mostly adipose tissue and connective tissue). The size of the subcutis is very variable in the individual person and between persons. When using spray injection it is difficult to estimate how much of the medicine glances off from the dead cells at the skin surface and how much actually reaches the subcutis.

BRIEF SUMMARY OF THE INVENTION

It is an object of the invention to provide an injection member for a jet spray injection device by which injection member the above mentioned drawbacks are overcome.

An injection member according to the invention is characterised in that it comprises a skin-penetrating member having a length in the range from 0.05 mm to 6 mm combined with a jet spray nozzle.

The use of the injection member according to the invention will reduce the risk of damaging the often very large medicine molecules during the passage through of the skin. Furthermore, less injection force needs to be applied and a more precise definition of the injection depth is possible so that superficial or too profound deposits is avoided. The size of the skin-penetrating member may be so small that it does not cause pain but is, if at all, felt as a small pressure on the skin. The risk for bleeding due to needle trauma is also reduced to almost zero.

According to the invention the skin-penetrating member may have a length in the range 0.05 mm to 4 mm, preferably between 0.3 mm and 2 mm. Such skin-penetrating members will be too short for conventional injection but may be used for jet injection to ensure that the jet has not to penetrate the stratum corneum.

In a preferred embodiment of the invention, the skin-penetrating member has a length from 0.05 mm to 0.3 mm, more preferred 0.1 mm to 0.2 mm. With this length the skin-penetrating member is long enough to weaken or penetrate the stratum corneum but not long enough to cause significant contact with the layer of living cells beneath stratum corneum, and insertion in the subcutis is impossible. Neither will the skin-penetrating member be able to get in contact with the sensory nerve endings located in the cutis. Medicine delivered as a jet through the skin-penetrating member will not partly glance off from the keratine layer, and thus the injected dose will be more accurate. Moreover the risk of pain release as seen with conventional subcutaneous needles will be minimized to that of the jet stream.

The shape of the skin-penetrating member may be that of a conventional needle, but it may have other forms and the peripheral end may be sharp or blunted. The inner diameter of the skin-penetrating member may be from 0.1 mm to 3 mm.

According to the invention the injection member may appropriately be a changeable unit which can be mounted on a jet injection syringe. This will allow the injection ember to be changed each time an injection has been made. Also the skin-penetrating member ay at each injection be chosen to have a length suited for the user and the intended point of injection.

By a number of measurements it is found that the thickness of the cutis and subcutis lies in the intervals described in the following table. The mean values may be seen as the values valid for the preferred injection zones.

|          | Females |      |      | Males |      |      |
|----------|---------|------|------|-------|------|------|
|          | min     | max  | mean | min   | max  | mean |
| cutis    | 1.1     | 3.6  | 1.7  | 1.2   | 4.1  | 2.3  |
| subcutis | 4.5     | 30.8 | 12.1 | 2.3   | 26.9 | 7.2  |
| sum      | 5.6     | 34.4 | 13.8 | 3.5   | 31.0 | 9.5  |

According to the invention the injection member may be provided with an array of short skin-penetrating members. Hereby a better distribution of the injected liquid is ensured.

BRIEF DESCRIPTION OF THE SEVERAL VIEWS OF THE DRAWING

In the following the invention is described in further details with references to the drawing, wherein.

DETAILED DESCRIPTION OF THE INVENTION

Figure 1:
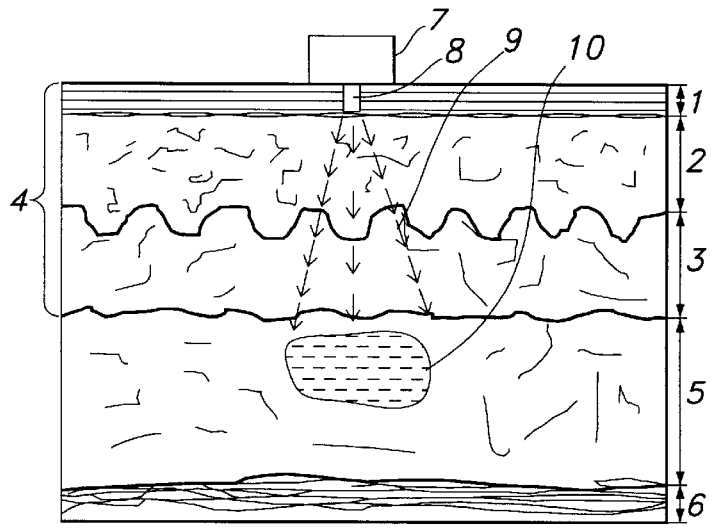
FIG. 1 schematically shows a sectional view of the skin during the injection of a liquid in a jet from an injection member according to the invention.

In FIG. 1 a keratin layer 1, i.e, the stratum corneum, overlies the epidermal 2 and dermal layers 3. These three layers form cutis, the skin, 4. Beneath this is subcutis 5 followed by a muscle 6 in its fascia.

An injection member 7 is pressed against the upper surface of the skin so that a skin-penetrating member 8 penetrates the keratin layer 1. From this position a jet 9 is expelled from the skin-penetrating member 8 at a speed allowing it to penetrate the remaining part of cutis and to intrude the subcutis 5 where it forms a deposit 10 which subsequently is taken up by the blood/lymph system. During its passage into subcutis 5 the jet 9 is decelerated so it will not penetrate the muscle fascia 6.

As the skin-penetrating member helps the jet to pass the cutis the jet need not be expelled with as high an energy content as needs a jet which must pierce the surface of the cutis. If an intramuscular injection is wanted the velocity and the pressure by which the jet is expelled must be correspondingly higher so that the liquid is not decelerated to an extend disabling its penetration ability until it has passed the muscle membrane 3.

Figure 2:
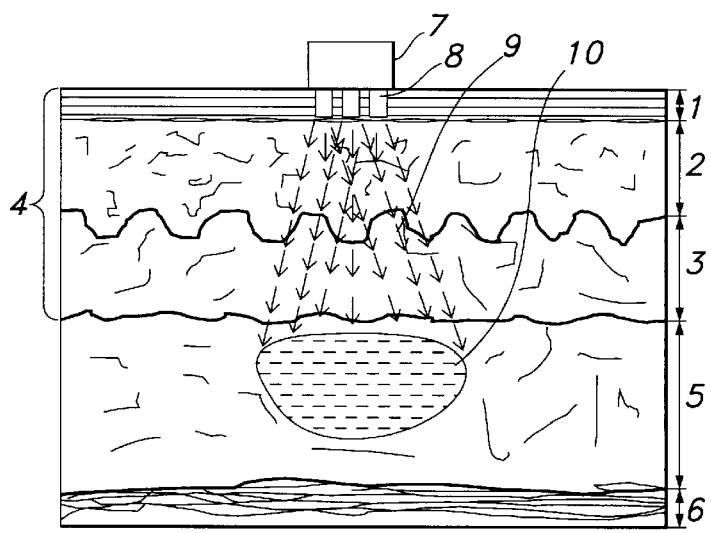
FIG. 2 shows schematically a sectional view of the skin during injection of a liquid in multiple jets from another embodiment of the injection member according to the invention.

In FIG. 2 elements corresponding to elements shown in FIG. 1 are given the same reference numbers. The injection member may be equipped with a number of skin-penetrating members. In the embodiment shown in FIG. 2 an injection member with three skin-penetrating members 8 are shown. By this dividing into more jets 9 a better distribution of the liquid in the subcutis is obtained. As the jets do not have to perform the initial penetration of the cutis surface a lower energy content in each jet will do and the output energy which may be supplied by an injector can be distributed to more jets.

Figure 3:
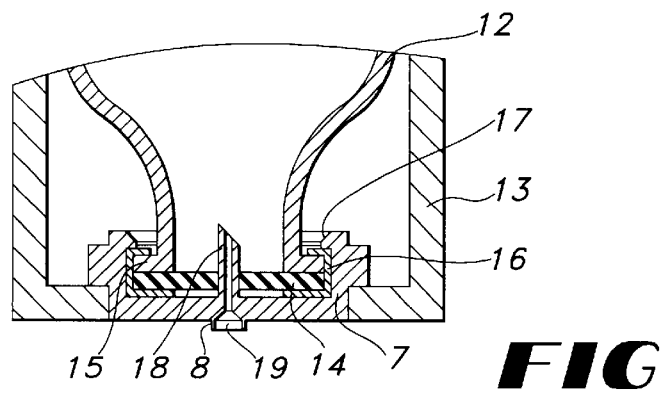
FIG. 3 is a schematic representation of a third embodiment of the invention.

FIG. 3 shows an injection member 7 mounted on a cartridge 12 in a housing 13 of an injection device. The cartridge 12 is closed by a rubber membrane 14 which is by a metal cap 16 clamped sealingly to a flange 15 forming an integral part of the cartridge 12. The injection member is clicked onto the ampoule by circular hook edge 17 gripping behind the flange 15. A skin-penetrating member 18 penetrates the membrane to establish communication between the inside of the cartridge and a nozzle 19 which is surrounded by a ring shaped or tubular skin-penetrating member 8. The injection member may be released from the ampoule by breaking the hook edge out of engagement with the flange, and the member may be replaced by a new injection member.

What is claimed is:

1. An injection member for use with a jet spray injection device for administering a subcutaneous or intramuscular dose of medicine, wherein said injection member comprises a surface which may be pressed against the skin of a patient, a jet spray nozzle, and a skin-penetrating member communicating with said nozzle for allowing a jet spray to pass through said skin-penetrating member into a patient, wherein said skin-penetrating member projects from said surface by a distance in the range of 0.05 mm and 0.3 mm, whereby when said skin-penetrating member is inserted into the skin of a patient, it passes at least substantially through the stratum corneum such that a jet spray exits said skin-penetrating member within, or at least near, the dermal layer of the skin.

2. An injection member according to claim 1, wherein said skin-penetrating member has a length in the range of 0.1 mm to 0.2 mm.

3. An injection member according to claim 2, wherein said injection member includes an engagement member for releasably mounting the injection member on a jet injection syringe so that said injection member is a changeable unit.

4. An injection member according to claim 3, wherein said injection member includes a plurality of jet spray nozzles and a skin-penetrating member associated with each said nozzle.

5. An injection member according to claim 2, wherein said injection member includes a plurality of jet spray nozzles and a skin-penetrating member associated with each said nozzle.

6. An injection member according to claim 1, wherein said injection member includes an engagement member for releasably mounting the injection member on a jet injection syringe so that said injection member is a changeable unit.

7. An injection member according to claim 6, wherein said injection member includes a plurality of jet spray nozzles and a skin-penetrating member associated with each said nozzle.

8. An injection member according to claim 1, wherein said injection member includes a plurality of jet spray nozzles and a skin-penetrating member associated with each said nozzle.

* * * * *